United States Patent
Kawada et al.

(10) Patent No.: US 7,285,777 B2
(45) Date of Patent: Oct. 23, 2007

(54) SAMPLE DIMENSION MEASURING METHOD AND SCANNING ELECTRON MICROSCOPE

(75) Inventors: Hiroki Kawada, Hitachinaka (JP); Takashi Iizumi, Hitachinaka (JP); Tadashi Otaka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 294 days.

(21) Appl. No.: 10/504,869

(22) PCT Filed: May 19, 2003

(86) PCT No.: PCT/JP03/06203

§ 371 (c)(1), (2), (4) Date: Jun. 28, 2005

(87) PCT Pub. No.: WO03/098149

PCT Pub. Date: Nov. 27, 2003

(65) Prior Publication Data

US 2005/0247876 A1 Nov. 10, 2005

(30) Foreign Application Priority Data

May 20, 2002 (JP) ............................ 2002-143960

(51) Int. Cl.
*H01J 37/28* (2006.01)
*G01N 23/225* (2006.01)
(52) U.S. Cl. .................. 250/307; 250/310; 324/751
(58) Field of Classification Search ............... 250/307, 250/310; 324/751
See application file for complete search history.

(56) References Cited

U.S. PATENT DOCUMENTS

| 7,045,782 B2 * | 5/2006 | Ikeda et al. ................. 250/310 |
| 2004/0051040 A1 * | 3/2004 | Nasu et al. ................. 250/310 |
| 2004/0084619 A1 * | 5/2004 | Hartig et al. ............... 250/307 |

FOREIGN PATENT DOCUMENTS

| JP | 02-159508 | 6/1990 |
| JP | 2-159508 | 6/1990 |
| JP | 7-63542 | 3/1995 |
| JP | 9-166428 | 6/1997 |
| JP | 09-166428 | 6/1997 |
| JP | 11-94531 | 4/1999 |
| JP | 11-237230 | 8/1999 |
| WO | WO 03/021186 A1 | 3/2003 |

* cited by examiner

*Primary Examiner*—Jack I. Berman
(74) *Attorney, Agent, or Firm*—McDermott Will & Emery LLP (57) ABSTRACT

An object of the present invention is to suppress measurement errors caused by the fact that the shrink amount due to scan of an electron beam differs pattern by pattern.

To accomplish this object, according to the invention, functions indicative of a process of change of pattern dimension when the electron beam is irradiated on a sample are prepared in respect of the kinds of sample patterns, and dimension values of a particular pattern measured by scanning the electron beam on the particular pattern are fitted to a function prepared for the particular pattern to calculate a dimension of the particular pattern before it changes.

13 Claims, 8 Drawing Sheets

| | Measurement Times | | |
|---|---|---|---|
| Calibration MP | Shrinkage Characteristics | | |

Calibration MP

| P.No. | MP Name | Times |
|---|---|---|
| 1 | Line130 | 2 |
| 2 | Space | 1 |
| 5 | Line150 | 3 |
| 6 | Line170 | 4 |

Shrinkage Characteristics

| | Measurement Times | Accuracy [nm] | Shrinkage [nm] |
|---|---|---|---|
| ◇ | 1 | 3.2 | -1.2 |
| ◇ | 2 | 1.9 | -1.8 |
| ◆ | 3 | 0.9 | -2.3 |
| ◇ | 4 | 0.7 | -2.7 |
| ◇ | 5 | 0.5 | -3.0 |
| ◇ | 6 | 0.5 | -3.1 |
| ◇ | 7 | 0.4 | -3.2 |

OK　　　　　　　　　　Cancel

FIG.8

SAMPLE DIMENSION MEASURING METHOD AND SCANNING ELECTRON MICROSCOPE

TECHNICAL FIELD

The present invention relates to a method of measuring dimensions of patterns by using a scanning electron microscope and to the scanning electron microscope and more particularly, to a measuring method having as an object to be measured a sample whose shape changes under irradiation of an electron beam and to the scanning electron microscope.

BACKGROUND ART

In a fabrication/inspection process of functional device products manufactured through surface fine working, such as semiconductor devices and thin film magnetic heads, a scanning electron microscope is widely used for finding the size of a worked pattern width (hereinafter called "measurement") and external appearance inspection.

The electron scanning microscope is an apparatus in which an electron beam emitted from an electron source and finely focused by means of focusing and objective lenses each utilizing an interaction of the electron beam with a magnetic or electric field is scanned one-dimensionally or two-dimensionally on a sample by using a deflector, a secondary signal generated from the sample by electron beam irradiation (secondary electrons, reflected electrons or electromagnetic waves) is detected with a detector utilizing the photoelectric effect and the detected signal is converted/processed into a visual signal such as a brightness signal synchronous with scanning of the electron beam to form a sample image.

In the scanning electron microscope, an effort is made to obtain a sample image highly accurately corresponding to the shape of a sample surface to be observed/measured and a distance between two arbitrary points on the sample surface is calculated from the thus obtained sample image. This calculation is generally called "measurement" and a scanning electron microscope having the calculation function as above is called a "measuring electron microscope".

Needless to say, in this type of scanning electron microscope, an electron beam having an arrival energy amount of several of hundreds of electron volts is irradiated on the surface of a sample to be observed.

Meanwhile, fine working of the surface of semiconductors has been further advanced in recent years and the use of photo resist reactive to argon fluoride (ArF) excimer laser light (hereinafter called "ArF resist") as a photolithography sensitive material has been started. The ArF laser light has a short wavelength of 160 nm and the ArF resist is therefore considered to be suitable for use in exposure of finer circuit patterns.

DISCLOSURE OF THE INVENTION

But results of latest studies have revealed that the aforementioned resist is very fragile to the electron beam irradiation and when a formed pattern is observed or measured with the scanning electron microscope, a base of acrylic resin, for instance, is found to undergo a condensation reaction under scanning of the focused electron beam and suffer from a reduction in volume (hereinafter called "shrink"), thereby changing the shape of the circuit pattern. Meanwhile, in semiconductor devices, the shape/dimension of a circuit pattern needs to be controlled stringently for the sake of materializing their design performance and to this end, the measuring electron microscope capable of measuring fine dimensions has been used in an inspection process.

In the event that a shrink takes place during the electron beam irradiation for measurement, there arises a problem that a dimension before the shrink becomes unknown. Further, in continuous measurement of the same site, the electron beam irradiation is repeated to change the line width, so that measured values disperse at individual measurement times, raising a problem that the measurement accuracy is degraded.

Any apparatus substituting for the measuring electron microscope capable of measuring fine dimensions at desired accuracies is unavailable and shrinkages of patterns due to the measurement make accurate dimensional values unknown, thus seriously bottlenecking in the semiconductor device fabrication using the ArF resist.

JP-A-11-237230 discloses that an approximate curve is calculated either from repeatedly measured values or the number of measurement times to presume dimensions at a measurement start time and at a desired measurement time in order that the influence due to contamination and charge-up phenomena can be reduced. But this reference considers neither suppressing the number of measurement times to a minimum to minimize the shrink of the ArF resist nor performing such automatic measurement as carried out in the semiconductor factory.

An object of the present invention is to provide dimensional value measurement method and apparatus suitable for performing measurement of patterns such as ArF resist liable to undergo shrinks by electron beam irradiation.

According to the invention, to accomplish the above object, a pattern dimension shrinkable under irradiation of an electron beam is measured and the thus measured values and an approximate function (approximate curve) indicative of progress of shrinks are used to presume a dimensional value before the shrinkage.

Figure 1:
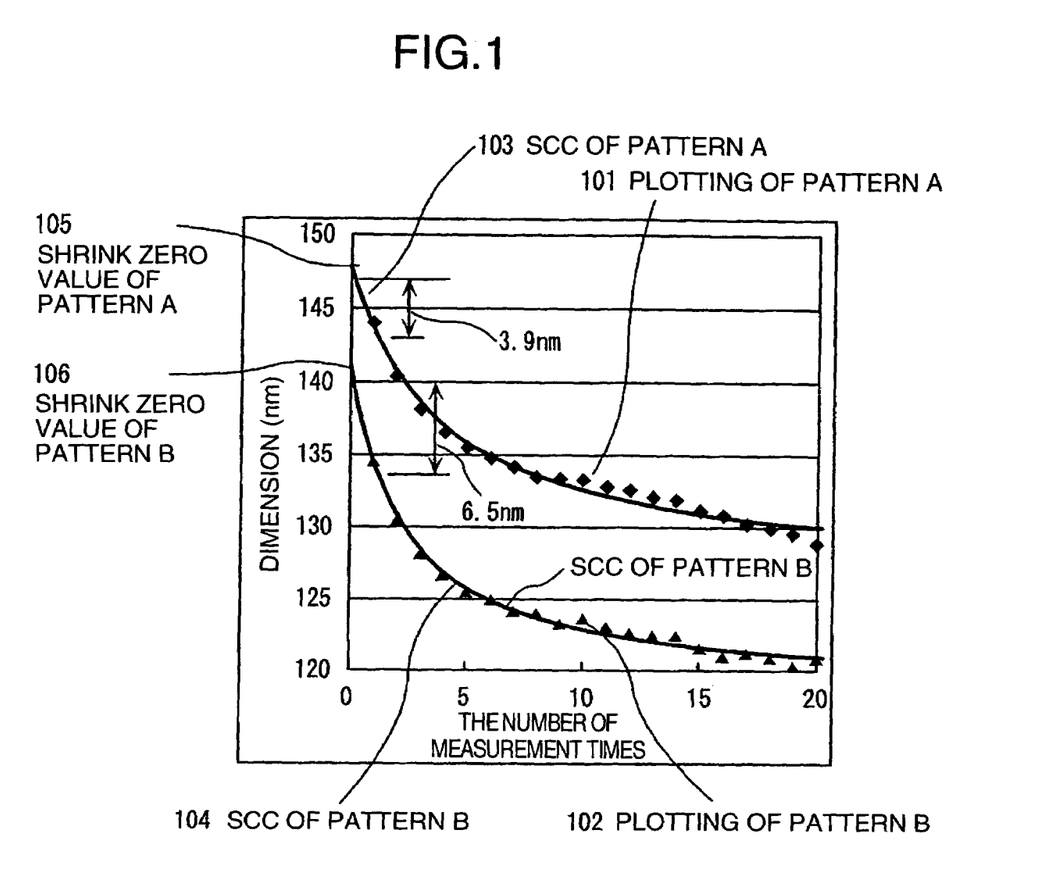
FIG. 1 is a diagram for explaining plots of shrunk patterns and SCC's.

By taking this approximate curve (hereinafter called "SCC (Shrink Characteristic-Curve) curve", for instance, data of experiments conducted by the inventors will be shown in FIG. 1.

SCC curves 103 and 104 are fitted to plotting 101 and plotting 102, respectively, which are obtained when patterns A and B of the same resist material and of the same surface shape but having different line widths are measured repeatedly.

Noticing first only the pattern A, it will be seen that the pattern is shrunk by an electron beam irradiated at an accelerating voltage of 800V and measured dimensions decrease as the number of measurement times increases.

A dimension before the electron beam is irradiated (hereinafter called "shrink zero dimension") can be presumed from a zero intercept of the approximate curve, that is, a dimension corresponding to zero of the number of measurement times.

The present invention provides a method of measuring a dimensional value of a pattern before its shrink by using the aforementioned SCC curve and the concrete contents of the invention can be understood from a description of best mode for carrying out the invention.

BEST MODE FOR CARRYING OUT THE INVENTION

Figure 6:
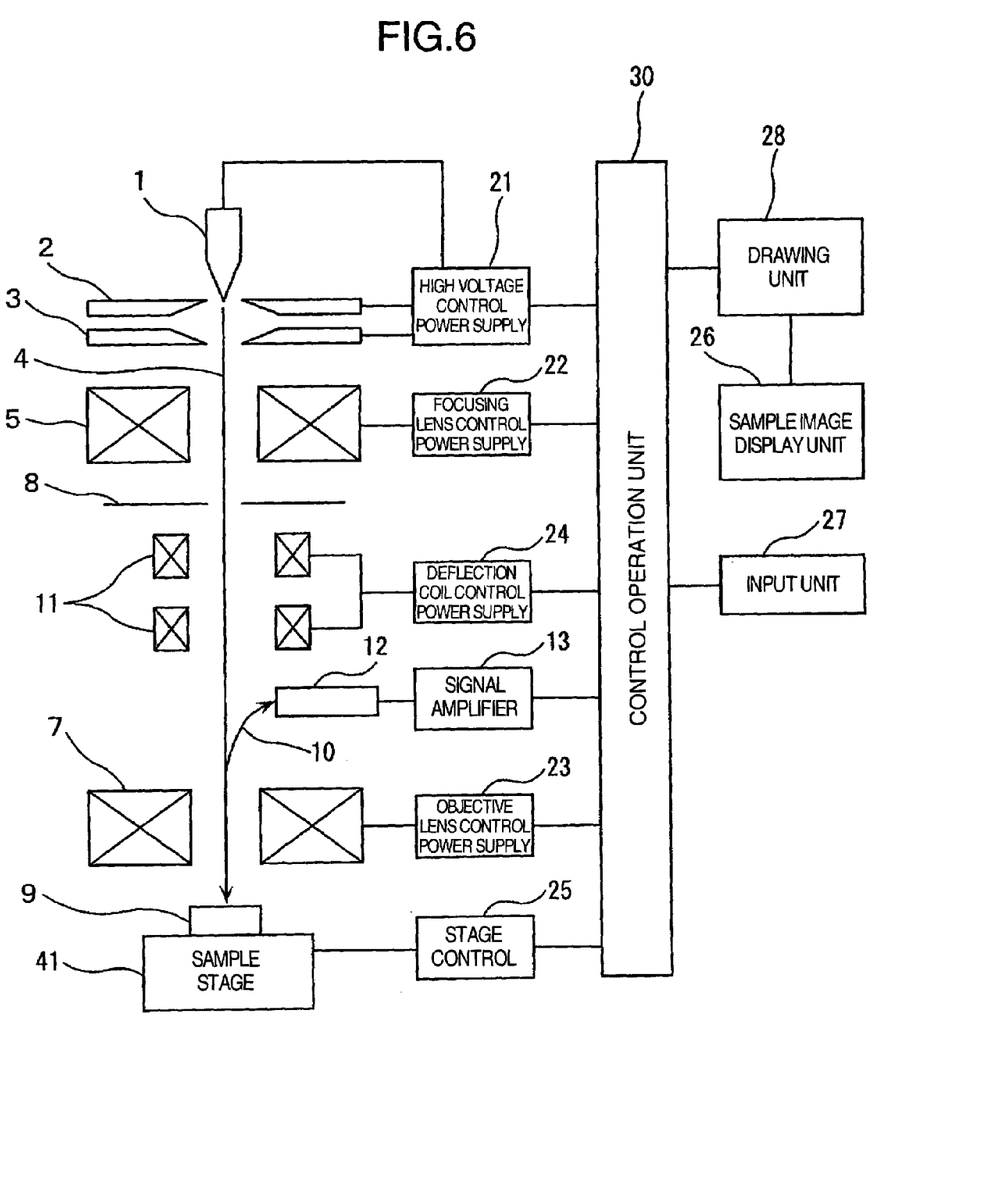
FIG. 6 is a diagram illustrative of the outline of a scanning electron microscope for carrying out the present invention.

FIG. 6 is a diagram showing the construction of a scanning electron microscope according to an embodiment of the invention. A voltage is applied across a cathode 1 and a first anode 2 by means of a high voltage control power supply 21 controlled by a control operation unit 30 (control processor) and a predetermined emission current is drawn out of the cathode 1. Since an accelerating voltage is applied across the cathode 1 and a second anode 3 by means of the high voltage control power supply 21 controlled by the control operation unit 30, a primary electron beam 4 emitted from the cathode 1 is accelerated to travel to a lens system of succeeding stage. The primary electron beam 4 is focused with a focusing lens 5 controlled by a focusing lens control power supply 22 and an unnecessary region of primary electron beam 4 is removed by means of an aperture plate 8.

Thereafter, the primary electron beam is focused into a small spot on a sample 9 by means of an objective lens 7 controlled by an objective lens control power supply 23 and is scanned two-dimensionally on the sample by the action of a deflection coil 11. A scanning signal of the deflection coil 11 is controlled in accordance with observation magnification by the action of a deflection coil control power supply 24. The sample 9, on the other hand, is fixedly mounted on a two-dimensionally movable sample stage 41. Movement of the sample stage 41 is controlled by means of a stage controller 25.

Secondary electrons 10 generated from the sample 9 by irradiation of the primary electron beam 4 are detected by a secondary electron detector 12 and a drawing unit 28 converts a detected secondary signal into a visual signal and controls the detected signal such that it is arranged suitably on another plane, with the result that an image corresponding to a surface shape of the sample can be displayed as a sample image on a sample image display unit 26.

An input unit 27 plays the role of an interface between an operator and the control operation unit 30 and the operator controls the aforementioned individual units and besides designates a measuring point and commands dimension measurement through the medium of the input unit 27. The control operation unit 30 is provided with a storage, not shown, and can store obtained measurement values and the measurement sequence to be described later.

The signal detected with the secondary electron detector 12 is amplified by a signal amplifier 13 and then accumulated in an image memory inside the drawing unit 28. While the apparatus of the present embodiment includes the secondary electron detector 12, this in not limitative and it may include a reflection electron detector for detection of reflected electrons or a detector for detection of light, electromagnetic wave or X-rays in place of the secondary electron detector or in combination therewith.

An address signal corresponding to a memory position in the image memory is generated in the control operation unit 30 or in a separately installed computer and is converted into an analog signal which in turn is supplied to the deflection coil 11. For example, when the image memory has 512×512 pixels, an address signal in X direction is a digital signal for repeating 0 to 512 and an address signal in Y direction is a digital signal for repeating 0 to 512 which is advanced by plus 1 when the address signal in X direction reaches from 0 to 512. These signals are converted into analog signals.

Addresses on the image memory correspond to addresses of the deflection signal for scanning the electron beam and therefore a two-dimensional image of a deflection region of electron beam by the scanning coil is recorded on the image memory. Signals in the image memory can be read out sequentially in time sequence by means of a read address generation circuit synchronized with a read clock. A signal read out in correspondence with an address is converted into an analog signal which in turn acts as a brightness modulation signal for the sample image display unit 26.

The image memory has a function to store an image (image data) by superimposing (synthesizing) it for the purpose of improving the S/N ratio. For example, by storing images obtained through 8 two-dimensional scanning operations while superimposing them, one complete image can be formed. In other words, images formed in a unit-of one or more X-Y scanning operations are synthesized to form an ultimate image. The number of images (frame cumulation number) for formation of one complete image can be set arbitrarily and a proper value is set in the light of a condition for secondary electron generation efficiency and the like. Also, by further superimposing a plurality of images formed through cumulation of plural images, an image desired to be obtained ultimately can be formed. By executing blanking of the primary electron beam at the time that a desired number of images are stored or after then, inputting of information to the image memory may be interrupted.

In a description to be given below in connection with the present embodiment, for performing one measurement operation, a predetermined number of images (for example, 8 images) are cumulated and information necessary for performing measurement (for example, line profile) is extracted therefrom. Namely, for conducting measurement plural times, (8×measurement times) images are acquired. The present embodiment will be described by way of example of measurement based on image formation but this in not limitative and for example, a line profile may be formed by scanning the electron beam one-dimensionally and grounding on detection of, for example, secondary electrons emitted from the scanned site.

In case where the frame cumulation number is set to 8, the sequence may be set according to which when a nine-th image is inputted, the first image is erased and eventually 8 images remain; or the weighted arithmetic mean may be carried out according to which when a nine-th image is inputted, a cumulated image stored in the image memory is multiplied by ⅞ and is then added with the nine-th image.

The apparatus according to the embodiment of the invention has also a function to form a line profile on the basis of detected secondary electrons or reflected electrons. The line profile can be formed on the basis of an amount of detected electrons or brightness information of a sample image when the primary electron beam is scanned one-dimensionally or two-dimensionally, and the thus obtained line profile can be used for dimension measurement of patterns formed on, for example, a semiconductor wafer.

In measuring dimensions of a pattern, two vertical or horizontal cursor lines are displayed together with a sample image on the sample image display unit 26, the two cursors are set to two edges of the pattern through the input unit 27 and a measured value is calculated as a dimensional value of the pattern by means of the control operation unit 30 on the basis of image magnification of the sample image and information of a distance between the two cursors.

In connection with FIG. 6, the control processor has been described as being integral with the scanning electron microscope or being its equivalency but this is in no way limitative and a process to be described below may be carried out with a control processor provided separately from the scanning electron microscope. In that case, there need a transmission medium for transmitting a detection signal detected by the secondary electron detector 12 to the control processor and signals from the control processor to the lenses and deflector of the scanning electron microscope and an input/output terminal for input/output of the signals to be transmitted via the transmission medium. Alternatively, a program for carrying out the process to be described below may be registered in a storage medium and the program may be executed by means of a control processor having an image memory and supplying necessary signals to the scanning electron microscope.

Further, the apparatus according to the present embodiment has a function to precedently store, as a recipe, conditions for observing, for example, a plurality of points on a semiconductor wafer (such as measuring sites and optical conditions of the scanning electron microscope) and perform measurement and observation in accordance with the recipe.

Further, a program for performing the process to be described below is registered in a storage medium and the program may be executed by means of the control processor having the image memory and supplying necessary signals to the scanning electron microscope. In other words, the embodiment of the invention to be described hereinafter can stand as an invention of a program adoptable to a charged particle beam apparatus such as scanning electron microscope provided with an image processor.

EMBODIMENT

In the present embodiment, a concrete example will be described which is adapted to solve problems explicitly arising in a technique of measuring pattern dimensions shrunk by irradiation of an electron beam and presuming a dimensional value before shrink by using measured values and an approximate function (approximate curve) indicative of progress of shrinkages.

In the first place, a problem is raised by the fact that the amount of shrink differs pattern by pattern. In actual measurement, the throughput of measurement must be maintained with a view to improving production efficiency and a shrink zero dimension must be determined by as small measurement times as possible. Accordingly, the manner requiring the number of measurement times up to 20 to determine the shrink zero dimension as in FIG. 1 is unprofitable for the measurement in production line.

Then, a way to presume a shrink zero value by adding a constant value to a measured value at a first time is conceivable but practically, it suffers from an excessively large error and is inexecutable. For example, a shrink zero value 105 of pattern A in FIG. 1 deviates from the first time measured value by 3.9 nm and for the pattern B, the deviation is 6.5 nm. Between the two patterns, the difference amounts up to 2.6 nm and this value is an excessively large value in a process for a dimension of 100 nm or less which needs to suppress the error to about 1 nm or less.

Under the circumstances, SCC's must be fitted to individual patterns so as to determine shrink zero values and to this end, a large number of measurement times are necessary. Although the larger the measurement times, the more the error tends to be small, the throughput is degraded concurrently. In other words, the trade-off relation exists between the error and the throughput. Accordingly, there arises a problem that how many measurement times at the least are needed to obtain a satisfactory error must be determined quantitatively.

To cope with this problem, the present embodiment proposes that in respect of individual patterns having different resist materials, exposure conditions, pattern shapes, pattern positions in wafer and distances to adjacent different pattern, sequence for calibration (hereinafter called "calibration measurement") be provided before the sequence of measurement for production management in production line (hereinafter called "routine measurement").

Namely, by using the same SCC curve for the same type of patterns, shrink zero values (namely, dimensions before patterns shrink) can be calculated on the basis of that SCC curve being apt to be equal for the same type patterns and accurate dimension measurement can be assured regardless of the variety of pattern types.

To add, sequence of storing SCC's for individual pattern types and automatically selecting an SCC on the basis of information about the type of a pattern selected by the input unit may be incorporated in the storage provided in the control operation unit 30 of the present embodiment apparatus shown in FIG. 6.

Further, sequence may be incorporated in which in addition to the SCC curves, proper measurement times are stored in respect of the individual types of patterns and when a pattern type is selected, a measurement time is set automatically.

In the routine measurement, a mathematic operation for fitting an SCC to measured values is carried out and besides, the same operation is also applied to the calibration measurement to determine an SCC function capable of minimizing the fitting error at that time.

By using this SCC function also in the succeeding routine measurement, the fitting error can be suppressed to a minimum. With a view to further improving the throughput by decreasing the number of calibration measurement times, a system and an enterprise form can be established which are adapted to supply SCC functions from an external database by communication routed through a network.

In the second place, a problem arises when the number of measurement times is desired to be reduced to suppress the shrink amount. In the event that a measured pattern is shrunk excessively, the pattern does not fulfill its function in a device, thus degrading the yield of production. Therefore, measurement needs to be executed while suppressing the shrink amount to as small a value as possible. Reducing the shrink amount, however, gives rise to a problem that the error in shrink zero value becomes large.

Figure 2:
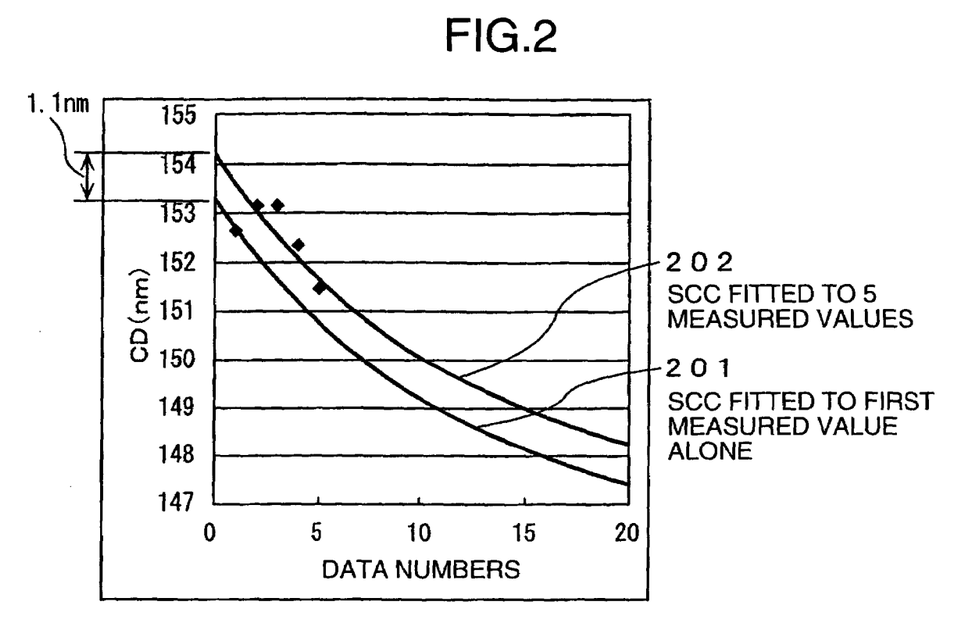
FIG. 2 is a diagram showing the principle of displacement of shrink zero dimension.

An example to this effect will be described using a graph of FIG. 2. Generally, measurement is carried out at an accelerating voltage of about 800V and if the voltage is suppressed to about 300V, the shrink amount can be suppressed but dispersion of measured values increases. In FIG. 2, a difference of 1.1 nm in shrink zero value occurs between an SCC 201 fitted to only the first measured value and an SCC 202 fitted to 5 measured values. In other words, the number of measured values to which the SCC is fitted changes the shrink zero value eventually, also leading to errors.

Then, for convergence of shrink zero value, the number of measurement times is preferably increased to make the curve fitted to a larger number of data pieces but in this case, the throughput decreases and the shrink amount increases. Therefore, it has been found that the error in shrink zero value is related to the throughput improvement and shrink amount suppression in trade-off relationship. Especially, when the accelerating voltage is lowered to decrease the shrink amount, dispersion of measured values increases and hence the above relation becomes remarkable. In using the shrink zero value for production management, a problem is found to arise in which errors in shrink zero value must be predicted quantitatively in respect of individual measurement times and a condition for making balance between the errors and the measurement times must be searched.

To solve this problem, how the error in shrink zero value changes with the measurement times is determined quantitatively through a mathematical method to be described later and minimized measurement times are selected under the restriction of the error and shrink amount. Such an operation as above is carried out after the SCC function is settled.

Through this, the measurement can be conducted by suppressing the error and shrink amount in routine measurement to permissible values or less and using a minimized number of measurement times, thereby making it possible to maximize the throughput.

A process flow of the embodiment of the invention will now be described with reference to the drawings.

Figure 3:
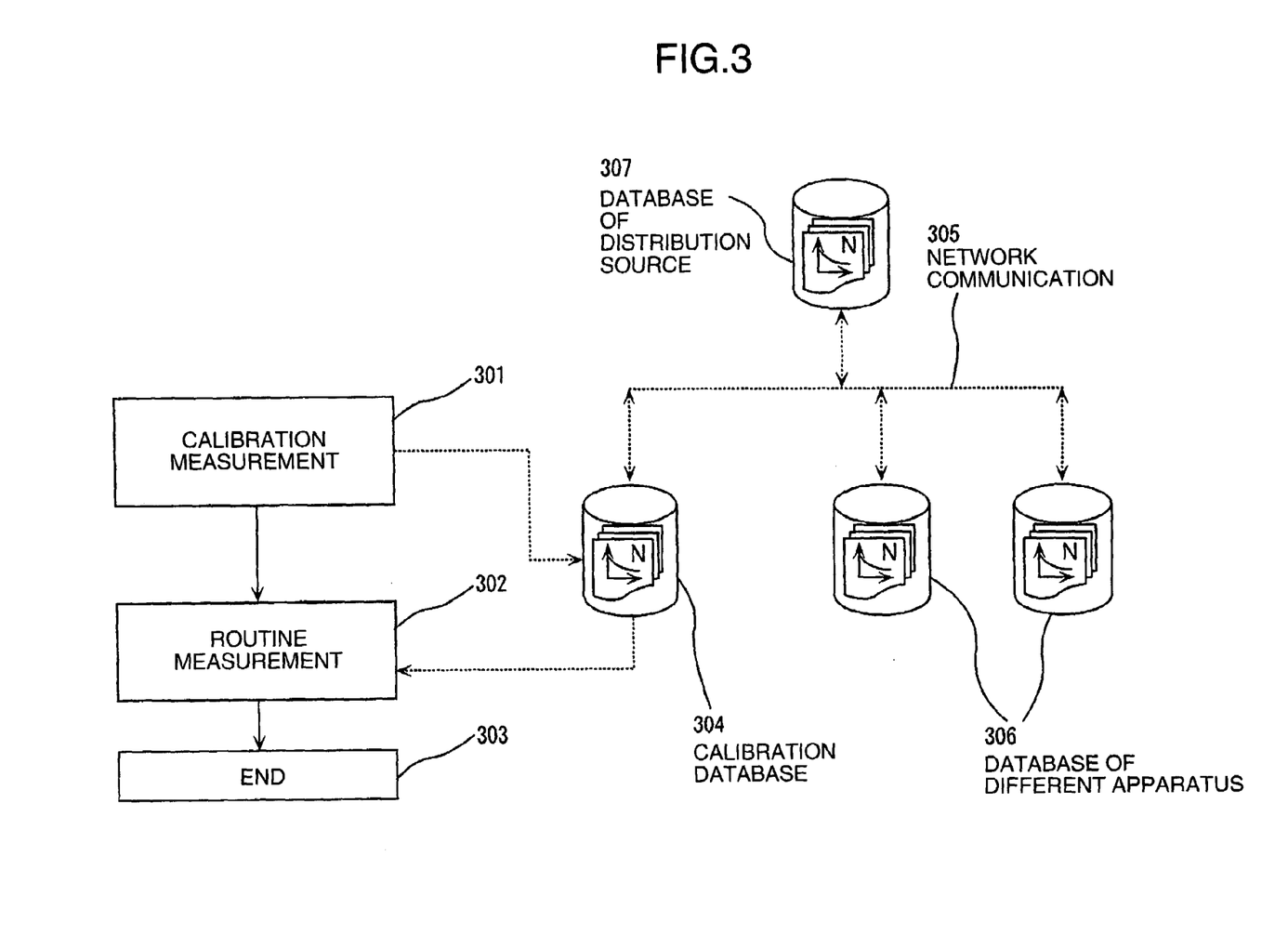
FIG. 3 is a diagram showing the flow of overall sequence of measuring a monitor pattern.

FIG. 3 shows, as an embodiment of the invention, a flow of the overall measurement sequence of a monitor pattern. A description will be given by taking an instance where measurement of a large number of wafers each coated with a resist material for ArF process and having the same exposure condition and pattern shape as well as the same pattern position in the wafer must be conducted.

One of these wafers is determined as a wafer for calibration and calibration measurement is carried out using this wafer.

For example, it is assumed that in the succeeding routine measurement, the production management is conducted by measuring a pattern common to all of the wafers (hereinafter referred to as "monitor pattern"). In that case, in calibration measurement 301, not only the monitor pattern but also a pattern considered to behave in shrinkage similarly to the monitor pattern is measured.

For example, a wafer subject to mass production is typically formed with a great number of devices of the same shape at plural sites. Accordingly, when 24 devices each having the same shape as a device including a monitor pattern are selected, 24 patterns each having the same pattern as the monitor pattern are selected. The thus selected patterns are measured in the way of calibration measurement and an SCC function indicative of shrink behavior of the monitor pattern is determined from measured data.

Then, this SCC function is used to quantitatively determine errors in shrink zero value in respect of individual measurement times pursuant to a calculation method to be described later. The results are presented to an operator to enable the operator to select measurement times by which the error and shrink amount can be below permissible values. Thus, calibration data including the selected measurement times and SCC function is forwarded to a calibration database 304 so as to be recorded thereon. Such working as above is also conducted in connection with a monitor pattern of a different shape, so that calibration data pieces can be accumulated in respect of various types of monitor patterns.

In routine measurement 302 shown in FIG. 3, calibration data necessary for measuring individual monitor patterns are read out of the calibration database and shrink zero dimensions are determined by using the read data.

Since it has already been confirmed in the calibration measurement 301 that the error in shrink zero value is within a permissible value or less, the error and the number of measurement times are within permissible values or less also in the routine measurement 302 in which an operation similar to that in the calibration measurement proceeds. Accordingly, the routine measurement 302 can be executed under the condition that the throughput is maximized and the shrink amount is minimized.

Incidentally, the calibration data is also allowed for being supplied from a resource other than the aforementioned calibration measurement 301. For example, as shown in FIG. 3, calibration data accumulated in databases 306 of different apparatus can be consulted through network communication 305. This permits the calibration measurement to be shared by a plurality of apparatus in the production line and therefore the process can be decreased in number as compared to the case where data is accumulated independently by separate apparatus, giving rise to an advantage that the production efficiency can be improved.

Also, an enterprise form for distributing calibration data is established so that data obtained from an apparatus dedicated to accumulation of data may be accumulated in a distribution source database 307 and calibration data may be distributed therefrom through the network 305, as necessary. With this scheme, a larger amount of data pieces can be accumulated using expenses supplied in the enterprise form and as a result, the process of calibration measurement in individual production lines can further be decreased in number to attain an advantage that the production efficiency can be improved. Details of each flow in FIG. 3 will be described hereunder.

Figure 4:
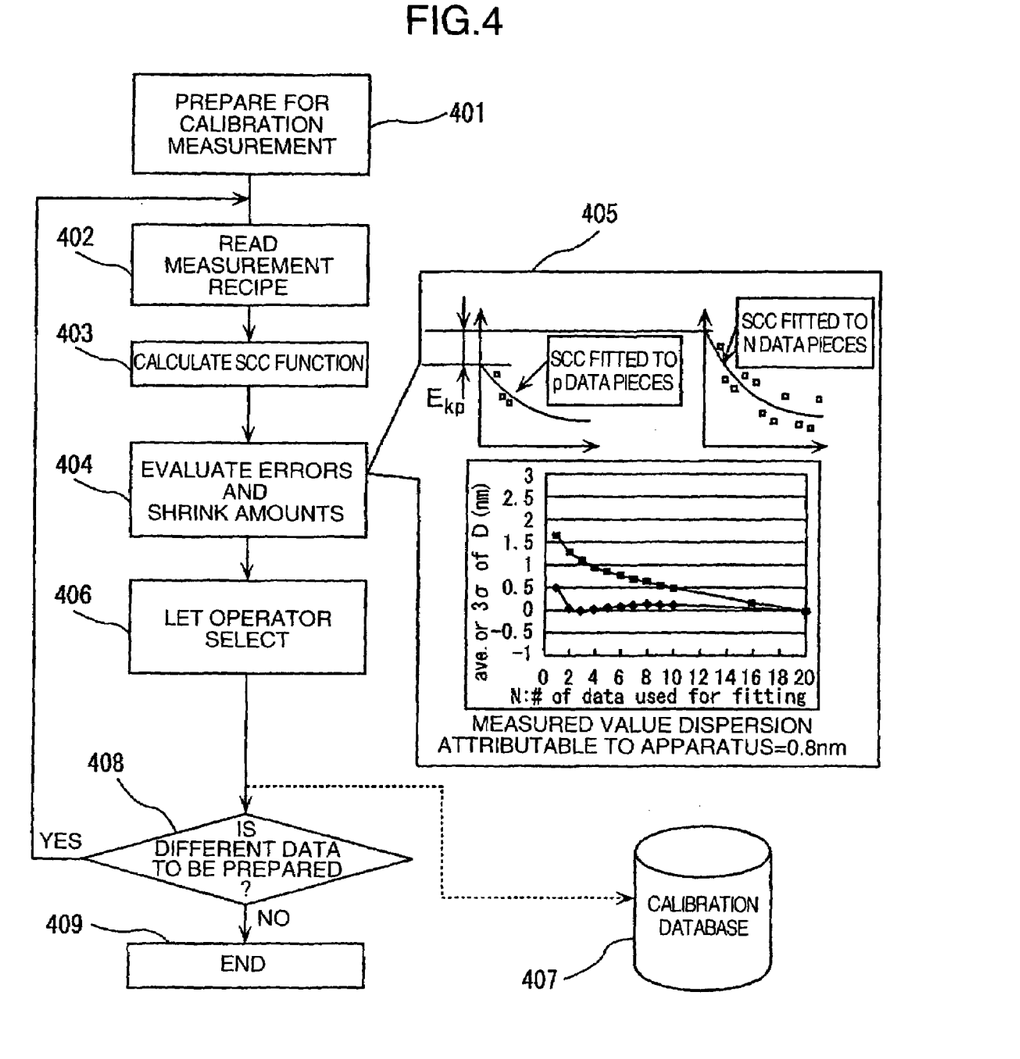
FIG. 4 is a diagram showing details of calibration measurement.

FIG. 4 shows details of calibration measurement in FIG. 3. In preparation 401 for calibration measurement, pre-preparation such as conveyance of a calibration wafer to a measurement position inside the apparatus is conducted.

Next, measurement recipe read routine 402 is executed. The measurement recipe includes information necessary for carrying out calibration measurement. As patterns to be measured, a monitor pattern and a pattern having shrink behavior similar to that of the monitor pattern are selected and such measurement conditions as positions on the wafer of the individual patterns, accelerating voltage and magnification during measurement and measurement times are involved. These pieces of information may be set in advance by the operator or may be determined automatically in accordance with the types of the wafer and monitor pattern to be measured.

Subsequently, SCC function calculation routine 403 is executed. Here, the individual patterns are first measured in accordance with the measurement recipe. As an example to be explained herein, the number of patterns to be measured in this routine is K and numbers 1 to K are assigned to the individual patterns. Measurement is carried out N times for the individual patterns. Assumptively, K=12 and N=20. In N data pieces obtained through measurement of the k-th pattern, n-th data from the start is indicated by $D_k(n)$. An SCC function determined through calculation in this routine is indicated by $F(n)$.

Then, $a_k$ and the SCC function $F(n)$ are fitted such that values of $a_k \cdot F(1)$, $a_k \cdot F(2)$, . . . , $a_k \cdot F(N)$ most approximate data pieces $D_k(1)$, $D_k(2)$, . . . , $D_k(20)$, respectively. Here, $a_k$ is similarity coefficient inherent to the k-th pattern.

In the following, a method of determining $a_k$ and $F(n)$ will be described by taking data of $k=1^{st}$ pattern, for instance. The accuracy of fitting can be evaluated by the value of variance $R_1^2$ defined as below.

$$R_1^2 = \frac{1}{N}[\{D_1(1) - a_1 \cdot F(1)\}^2 + \{D_1(2) - a_1 \cdot F(2)\}^2 + \ldots] \quad (1)$$

$$R_1^2 = \frac{1}{N}\sum_{n=1}^{N}[D_1(n) - a_1 \cdot F(n)]^2 \quad (2)$$

When the accuracy of fitting is maximized, the aforementioned $R_1^2$ is minimized and at that time, $\partial R_1^2/\partial a_1 = 0$ stands. This is applied to equation (1) to obtain $$a_1 = \frac{D_1(1) \cdot F(1) + D_1(2) \cdot F(2) + \ldots}{F(1)^2 + F(2)^2 + \ldots} \quad (3)$$

$$a_1 = \frac{\sum_{n=1}^{N} D_1(n) \cdot F(n)}{\sum_{n=1}^{N} F(n)^2} \quad (4)$$

In this manner, $a_1$ for maximizing the fitting accuracy can be determined.

Similarly, $a_k$ for the individual $1^{st}$ to k-th patterns is determined by the following equation:

$$a_k = \frac{\sum_{n=1}^{N} D_1(n) \cdot F(n)}{\sum_{n=1}^{N} F(n)^2} \quad (5)$$

At that time, mean value S of $R_1^2, R_2^2, \ldots, R_K^2$ is given by $$S = \frac{1}{K}\sum_{k=1}^{K} R_k^2 = \frac{1}{K}\sum_{k=1}^{K}\sqrt{\frac{1}{N}\sum_{n=1}^{N}[D_k(n) - a_k \cdot F(n)]^2} \quad (6)$$

By making S minimum, $F(n)$ being common to all of the patterns and maximizing the fitting accuracy can be determined.

This $F(n)$ provides so-to-speak values which differ from measured values at a plurality of sites by a predetermined value or less in the individual measurement times. In other words, that value makes the degree of variance from k measured values the predetermined value or less in the individual measurement times 1 to n. According to the above technique, an SCC curve averaged at individual measuring sites can be formed, thus making it possible to improve the accuracy of shrink amount calculation.

Here, for example, $$F(n) = \alpha \cdot \exp(\beta \cdot n + \gamma) \quad (7)$$

is used as $F(n)$. By changing parameters $\alpha$, $\beta$ and $\gamma$ by slight amounts, respectively, such that S can be minimized, $F(n)$ is determined. In this step, the SCC curve is so changed as to contour measured values at plural times. Through the step as above, a highly accurate SCC curve can be prepared which more approximates actual measurement results.

Next, evaluation routine 404 of the error and shrink amount is executed. In the previous routine, $a_k \cdot F(n)$ is fitted to 20 measurement data pieces in respect of each pattern but in the present step, errors and shrink amounts are determined when fitting is carried out using less amounts of measurement data pieces.

It is now assumed that shrink zero value $Z_{kN}$ determined in the k-th pattern by using N data pieces is $$Z_{kN} = a_k \cdot F(0) \quad (8)$$

Assumptively, N is a sufficiently large value and even if it is more increased, the value of $Z_{kN}$ converges to the range of less than measuring accuracy of the apparatus. In this case, $Z_{kN}$ can be deemed to be a truth value of shrink zero value.

On the other hand, it is assumed that shrink zero value $Z_{kp}$ determined using p data pieces from the start is $$Z_{kp} = a_{kp} \cdot F(0) \quad (9)$$

At that time, error $E_{kp}$ of $Z_{kp}$ is $$E_{kP} = |Z_{kN} - Z_{kp}| \quad (10)$$

On the assumption that $E_{1p}, E_{2p}, \ldots, E_{kp}$ thus determined are averaged to have mean value $M(E_{kp})$ and standard deviation $\sigma (E_{kp})$, data pieces are plotted in relation to p to obtain graphs displayed on the screen. An example of the display is indicated at 405. These graphs show how much the error $E_{kp}$ in shrink zero value can be reduced as the number of measurement times increases. By watching these graphs, the operator of the apparatus decides how many times the measurement is to be carried out at the least to suppress the error to a permissible level or less and determines necessary measurement times. In another graph of FIG. 4, values of $M(E_{kp})$ and values of 3 $\sigma (E_{kp})$ are plotted in relation to measurement times. Here, it is indicated that with the measurement times being 2, the $M(E_{kp})$ and 3· $\sigma (E_{kp})$ are both less than 1 nm permissible value and therefore, the operator selects measurement times of 2. This is done in routine 406.

Figure 7:
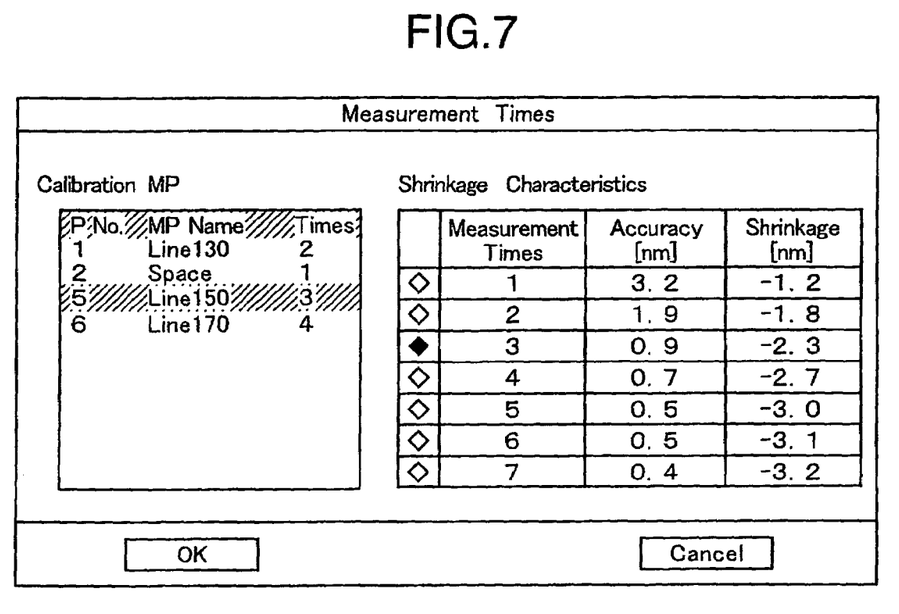
FIG. 7 is a diagram showing an example of display screen for selecting measurement times in an apparatus of the present embodiment.

FIG. 7 is a diagram showing an example of display screen for selecting the measurement times. In this display screen, deformation amounts of a pattern and measurement errors (accuracies) are displayed in combination in relation to measurement times. According to the display screen as above, the number of measurement times can be determined by making reference to measurement errors and pattern deformation amounts. In addition, on the left side of the screen, a window is provided through which the types of patterns can be selected. When the type of pattern is selected in the window, measurement errors and deformation amounts in relation to the measurement times are displayed in respect of each type of pattern and the measurement times for each type of pattern can be registered.

To add, when in the display example of FIG. 7, improvements in accuracy of measurement error are preferential and the pattern deformation amount does not matter so much, only the measurement times and measurement errors can be displayed. On the other hand, in case the pattern deformation is desired to be suppressed at the sacrifice of the measurement error to a certain extent, only the measurement times and pattern deformation amount can be displayed.

With the above construction, the relation between the measurement times and the accuracy of shrink zero value can be determined quantitatively. Accordingly, the accuracy can be maintained to a permissible level or more and minimum measurement times can suffice. In other words, since the relation between the throughput of measurement and the shrink amount of pattern after measurement can be grasped quantitatively, measurement conditions most preferable from the standpoint of the production efficiency and yield can be determined.

Also, at that time, the mean value S of $R_1^2, R_2^2, \ldots, R_K^2$ defined by equation (6) may be indicated beneath 405. The value of average S indicates dispersion of measured values from the curve representing the shrink amounts. In the dispersion, the influence of shrink is subtracted and dispersion of measured values attributable to the apparatus can be known. Here, the apparatus attribution is caused by factors such as for example changes in accelerating voltage and vibrations of the apparatus which are responsible for decreasing the signal/noise ratio of measured values. The effect attained by exhibiting the parameter will be described.

For example, studied herein is the difference from the technique of managing dispersion of measured values attributable to the apparatus by merely measuring only one pattern about 10 times, for example, and using 3 σ of dispersion of 10 measured values.

This technique does not matter when the shrink amount of pattern is negligibly smaller than dispersion of measured value attributable to the apparatus. However, when the shrink amount approximates or exceeds the width of dispersion of measured values, the shrink amount contained in the dispersion of measured values cannot be neglected, making it difficult to manage the dispersion attributable to the apparatus.

Especially, in order to reduce the shrink amount, measures are taken to decrease current of an electron beam and accelerating voltage for measurement but then, the signal/noise ratio of measured values is decreased to make the dispersion of measured value approximate to the shrink amount and this problem sometimes becomes remarkable.

Accordingly, by managing the dispersion attributable to the apparatus by means of the S as in the case of the present embodiment, even when the dispersion of measured values grows owing to variations in accelerating voltage caused by some reasons, the dispersion can be known by separating it from the influence of shrink and hence stability of the apparatus can advantageously be managed more highly accurately. Further, by periodically carrying out the calibration measurement including the present method, not only stability of the apparatus can be checked periodically but also unstableness of shrink status can be monitored by monitoring changes in F(n) and so the distribution of resist coated thickness on the surface and changes in resist exposure conditions can be perceived, thereby attaining an advantage that the results can be fedback to the resist coating machine and exposing unit to control them.

Thereafter, the selected number of measurement times $P_0$ and the used SCC function F(n) are recorded on a calibration database 407.

Similar working is executed for differently dimensioned and shaped patterns to be measured in the later routine measurement. Such a case is decided in 408 and the program is returned to 401.

The above procedures are carried out in respect of individual patterns having different resist materials, exposure conditions, shapes and in-device positions. In other words, the procedures are applied to individual patterns of the types to be measured in the succeeding routine measurement which are expected to be different in shrink status from each other.

Incidentally, the calibration measurement may be conducted periodically or when changes of process are predicted. Through this, even if the exposure condition, for instance, changes to change the SCC function, the changes can be corrected to maintain the accuracy.

Figure 5:
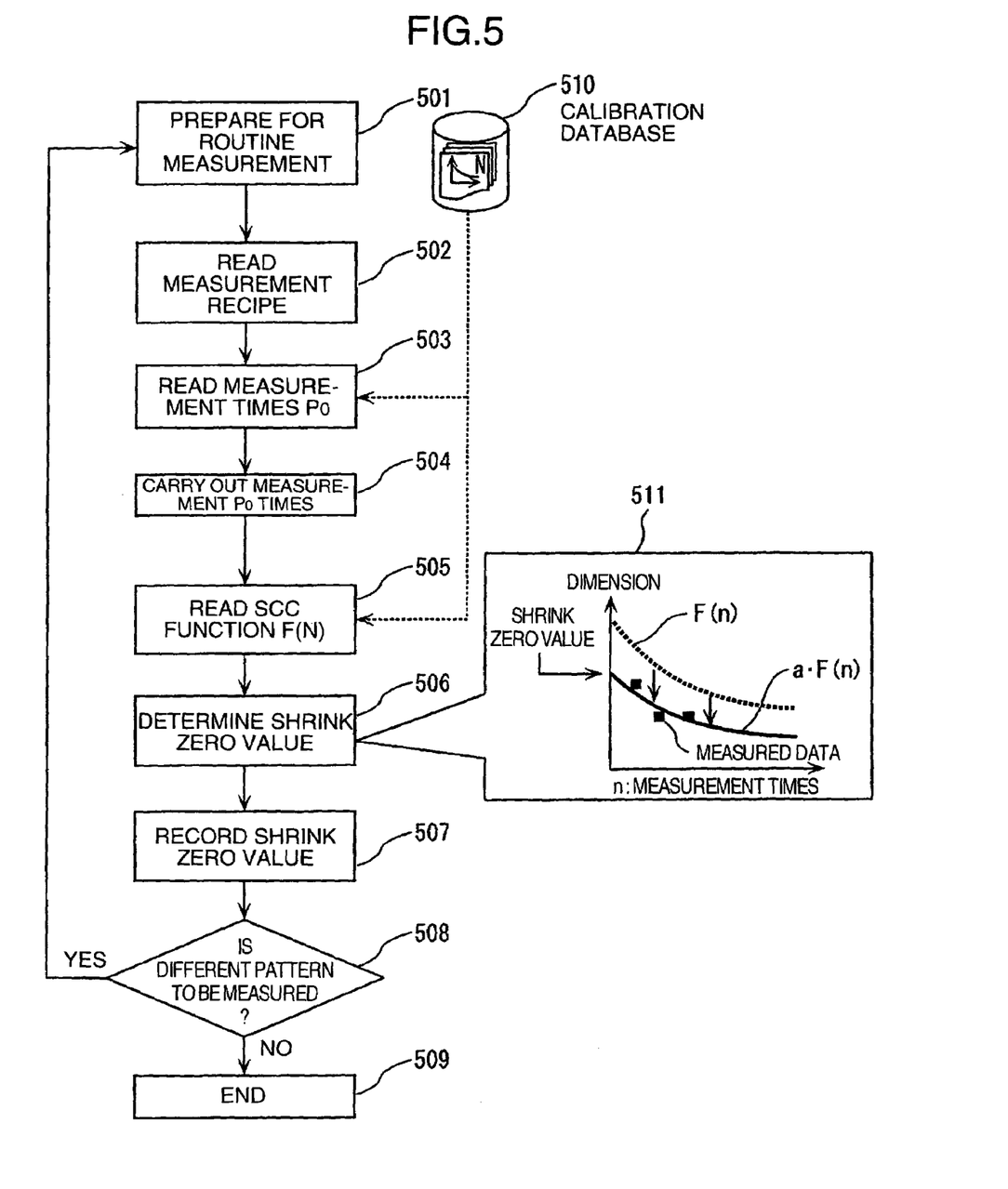
FIG. 5 is a diagram showing details of routine measurement.

Next, details of the routine measurement will be described with reference to FIG. 5. Firstly, preparation 501 for routine measurement is executed to perform pre-preparation such as conveyance of a wafer to a measuring position in the apparatus.

Subsequently, recipe read routine 502 is conducted. A recipe including measurement conditions for a pattern to be measured from now is read.

Next, measurement times $P_0$ are read. In the calibration measurement carried out precedently, the measurement times $P_0$ and SCC function F(n) suitable for the pattern to be measured from now have been determined. The measurement times $P_0$ are read out of a calibration database 510. Which one of $P_0$'s in the database is to be selected may be described in, for example, the recipe or may be determined by deciding the pattern shape automatically.

Then the pattern is measured $P_0$ times in 504. Here, the measured data pieces are designated by $D(1), D(2), \ldots, D(P_0)$ in order of measurement operations. Thereafter, SCC function read 505 is executed. An SCC function F(n) suitable for the measured pattern is read out of the calibration database 510.

Subsequently, the shrink zero value is determined in 506. Details of calculation in this routine will be explained. Like calculation conducted in connection with equations (3) and (4), $a \cdot F(1), a \cdot F(2), \ldots, a \cdot F(P_0)$ approximate $D(1), D(2), \ldots, D(P_0)$, respectively, where a is similarity coefficient, when $$a = \frac{\sum_{n=1}^{N_f} D(n) \cdot F(n)}{\sum_{n=1}^{N_f} F(n)^2} \tag{11}$$

stands. Then, shrink zero value $Z(P_0)$ at that time is $$Z(P_0) = a \cdot F(0) \tag{12}$$

An example where F(N) is fitted to data pieces obtained through 3-times measurement is shown at 511.

In the calibration measurement, 12 patterns having resist materials, exposure conditions, shapes and in-device positions equivalent to those of the pattern now measured have been measured and shrink zero values of the individual patterns have already been determined in accordance with calculation methods identical to equations (11) and (12). Therefore, an error in $Z(P_0)$ can be deemed to be equal to the error $3 \cdot \sigma (E_{kp})$ determined in the calibration measurement. In this manner, truth values and accuracies of the shrink zero value can be obtained as statistically reliable values and therefore, the present invention is effective in development of lithography process in which the absolute value of dimension before shrink needs to be managed and in mass production of devices.

Thereafter, recording of shrink zero value 507 is executed and $Z(P_0)$ is recorded as the measured value of the pattern. By recording the accuracy 3· σ ($E_{kNf}$) in combination, reliability of each measured value can also be evaluated later to advantage.

Then, "Is a different pattern to be measured ?" 508 is decided and if "Yes", the program returns to 501 to execute the routine measurement procedures set forth so far for the different pattern but if "No", the routine measurement ends in 509.

Incidentally, when many types of resist materials must be measured in dimension, the time required for calibration measurement necessary to prepare shrink curves increases and the production efficiency is degraded. In such a case, a method is available in which the calibration measurement is not carried out but instead, the shrink curve is prepared in the routine measurement.

Figure 8:
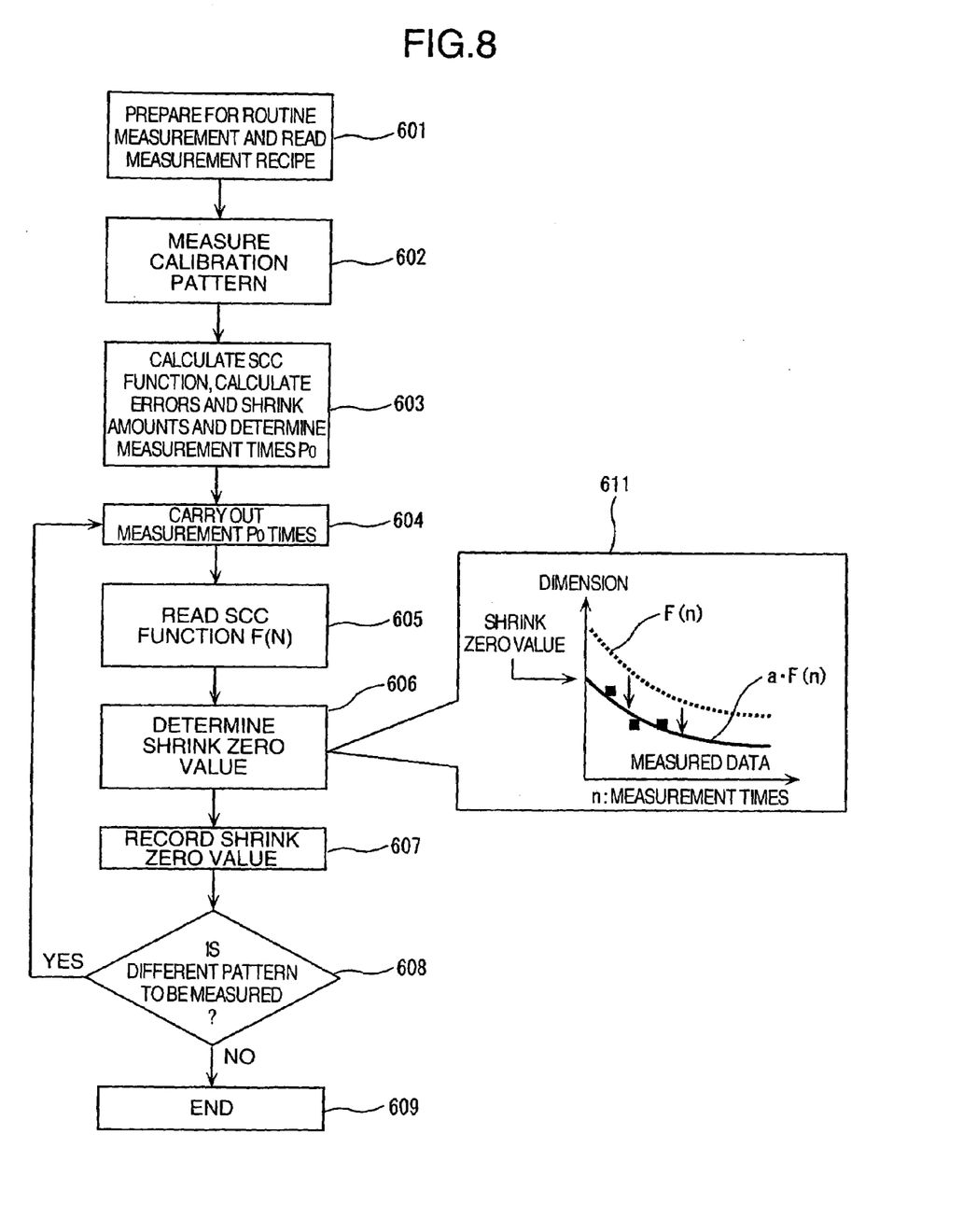
FIG. 8 is a diagram showing procedures for preparing a shrink curve in the routine measurement.

Concrete procedures in the method will be described with reference to FIG. 8. One or plural portions on a wafer not subjected to calibration measurement and formed with patterns to be measured are deemed to be calibration patterns and these patterns are measured, for example, 20 times (602).

By using this data, an SCC function is prepared (603). The calibration pattern may be, for example, a pattern prepared in advance and dedicated to calibration. Alternatively, a specified chip may be used exclusively for calibration. The ensuing procedure is the same as that in the case of the routine measurement described so far.

According to the aforementioned method, there is no need of carrying out calibration measurement operations and preparing databases separately.

Accordingly, even when any type of wafer is conveyed to the measurement process, it can be handled flexibly, giving rise to improvements in productivity.

The employment of this method ensures a newly attainable merit. As the time elapses after the resist is coated on a wafer, the shrinkage characteristics of the resist sometimes change. This is because solvent in the resist has vaporized or conversely ammonia contained in atmosphere by a slight amount is trapped in the resist to neutralize acid substance. Under the circumstances, the shrinkage characteristics of the resist change with the lapse of time, so that even if the calibration measurement is carried out separately, an SCC function obtained therethrough does not coincide with the shrinkage characteristics used for actual measurement, leading to errors.

But, with the employment of this method, the shrink curve can be determined immediately before measurement and hence a new advantage that the problem of temporal change of shrink curve does not occur can be obtained.

The foregoing description of the embodiment of the invention has been given by way of a pattern such as a line pattern which reduces in dimension value under irradiation of an electron beam but the measurement object pattern is not limited thereto. A space portion between line patterns and a contact hole pattern increase in dimensional value under irradiation of an electron beam. More particularly, the object sample contracts but the dimensional value increases. The method of the present embodiment can also be applicable to such a pattern and in such a case, a function is prepared in which the dimensional value increases as the number of measurement times increases and by performing the process described so far, the effect of the invention can be attained.

As described above, according to the invention, even with a pattern liable to shrink, its dimensional value before it shrinks can be measured accurately.

The invention claimed is:

1. A sample dimension measuring method for scanning an electron beam on a sample and measuring dimensions of patterns formed on said sample on the basis of detection of electrons emitted from the scanned site,
   wherein functions indicative of a transition of changes in dimension of said patterns when the electron beam is irradiated on said sample are prepared in accordance with the types of said patterns, and dimension values of a specified pattern measured by scanning said pattern with said electron beam are fitted to a function prepared for said specified pattern to calculate a dimension of said specified pattern before it changes.

2. A scanning electron microscope having an electron source, a focusing lens for focusing an electron beam emitted from said electron source, a scan deflector for scanning said electron beam on a sample, a detector for detecting electrons emitted from said sample, and an operation unit for measuring dimensions of patterns on said sample on the basis of the output of said detector,
   comprising an input unit for inputting the types of said patterns,
   wherein said operation unit has a storage medium for storing, in accordance with the types of said patterns, functions indicative of a transition of changes in dimension of said patterns when the electron beam is irradiated on said sample,
   fits dimension values of a pattern measured on the basis of electrons detected through scanning of said electron beam to a function corresponding to the type of said pattern inputted by means of said input unit to calculate a dimension of said pattern before it changes.

3. A scanning electron microscope according to claim 2, wherein said operation unit has a storage medium for storing the number of measurement times by said electron beam in accordance with the types of said patterns, and
   measures a pattern by the number of measurement times corresponding to the type of said pattern inputted by means of said input unit.

4. A scanning electron microscope according to claim 2, wherein said storage medium stores, in relation to measurement times, deformation amounts and/or measurement error amounts of patterns in respect of the individual types of said patterns.

5. A sample dimension measuring method for scanning an electron beam on a sample and measuring dimensions of patterns formed on said sample on the basis of detection of electrons emitted from the scanned sites,
   wherein measured values of a pattern dimension obtained in accordance with the number of measurement times corresponding to the type of said sample are fitted to a function indicative of a transition of changes in said pattern dimension when the electron beam is irradiated on said sample to calculate a dimension before said pattern changes.

6. A scanning electron microscope having an electron source, a focusing lens for focusing an electron beam emitted from said electron source, a scan deflector for scanning said electron beam on a sample, a detector for detecting electrons emitted from said sample, and an operation unit for measuring dimensions of patterns on said sample on the basis of the output of said detector, comprising an input unit for inputting the types of said patterns, wherein said operation unit has a storage medium for storing measurement times according to the type of said sample and functions indicative of a transition of changes in said pattern dimensions when the electron beam is irradiated on said sample, and performs measurement by the number of measurement times inputted by means of said input unit and fits measured values to a function indicative of a transition of decreases or increases in a pattern when the electron beam is irradiated on said sample to calculate a dimension of said pattern before it changes.

7. A sample dimension measuring method for scanning an electron beam on a sample and measuring dimensions of patterns formed on said sample on the basis of detection of electrons emitted from the scanned sites, comprising:

a step of measuring patterns at a plurality of different sites plural times; and a step of preparing, on the basis of a value which differs from a measured value at each of the plural sites at each measurement time by a predetermined value or less, a function indicative of changes in measured values in relation to change of the number of measurement times.

8. A sample dimension measuring method according to claim 7, wherein the measured values of a pattern are fitted to said prepared function to calculate a dimension of said pattern before it changes.

9. A scanning electron microscope comprising an electron source, a focusing lens for focusing an electron beam emitted from said electron source, a scan deflector for scanning said electron beam on a sample, a detector for detecting electrons emitted from said sample, and an operation unit for measuring dimensions of patterns on said sample on the basis of the output of said detector, wherein said operation unit includes a storage medium for storing measured values obtained when patterns at plural sites on said sample are measured plural measurement times, and prepares, on the basis of a value which differs from a measured value at each of the plural sites at each measurement time by a predetermined value or less, a function indicative of changes in measured values in relation to change of the number of measurement times.

10. A sample dimension measuring method for scanning an electron beam on a sample and measuring dimensions of patterns formed on said sample on the basis of detection of electrons emitted from the scanned sites, comprising:

a step of measuring a pattern plural times;

a step of changing a function indicative of change of dimension of said pattern by the electron beam in relation to measurement times such that the function contours plural measured values measured in the measuring step; and a step of calculating a measured value of said pattern before it changes on the basis of a function after the change.

11. A scanning electron microscope comprising an electron source, a focusing lens for focusing an electron beam emitted from said electron source, a scan deflector for scanning said electron beam on a sample, a detector for detecting electrons emitted from said sample, and an operation unit for measuring dimensions of patterns on said sample on the basis of outputs of said detector, wherein said operation unit includes a memory medium for storing a function indicative of change of dimension of a pattern when the electron beam is irradiated on said sample, whereby said function is so changed as to contour change of measured values obtained when said pattern is measured plural times.

12. A sample dimension measuring method for scanning an electron beam on a sample and measuring dimensions of patterns formed on said sample on the basis of detection of electrons emitted from the scanned sites, wherein deformation amounts of a pattern and/or measurement errors in relation to measurement times of said pattern is determined in advance; and a measurement frequency of said pattern is determined on the basis of a permissible deformation amount of pattern and a permissible measurement error and the dimension of said pattern is measured by the determined measurement times.

13. A scanning electron microscope having an electron source, a focusing lens for focusing an electron beam emitted from said electron source, a scan deflector for scanning said electron beam on a sample, a detector for detecting electrons emitted from said sample, and an operation unit for measuring dimensions of patterns on said sample on the basis of outputs of said detector, comprising:

display unit for displaying deformation amounts of a pattern and/or measurement errors in relation to measurement times of said pattern; and an input unit for designating a measurement frequency of said pattern, wherein said operation unit measures said pattern by said inputted measurement frequency and fits plural measured values to a function indicative of a process of decrease of said pattern dimension when the electron beam is irradiated on said sample to calculate a dimension of said pattern before it decreases.

* * * * *